United States Patent [19]

Bekkering

[11] 4,447,231

[45] May 8, 1984

[54] AUTOMATIC INJECTION SYRINGE

[75] Inventor: Hendrik M. Bekkering, Olst, Netherlands

[73] Assignee: Duphar International Research B.V., Weesp, Netherlands

[21] Appl. No.: 400,970

[22] Filed: Jul. 22, 1982

[30] Foreign Application Priority Data

Jul. 27, 1981 [NL] Netherlands .......................... 8103531

[51] Int. Cl.³ .............................................. A61M 5/00
[52] U.S. Cl. ..................................... 604/131; 604/226
[58] Field of Search ............. 604/57, 89, 92, 134–139, 604/141, 187, 226, 131, 132; 206/363, 364, 370, 206/438

[56]    References Cited
        U.S. PATENT DOCUMENTS

| 914,871 | 3/1909 | Ong ....................................... 604/92 |
| 2,541,621 | 2/1951 | Thompson ............................ 604/92 |
| 4,031,893 | 6/1977 | Kaplan et al. ....................... 604/136 |

Primary Examiner—John D. Yasko

Attorney, Agent, or Firm—Stevens, Davis, Miller & Mosher

[57] ABSTRACT

The invention relates to an automatic syringe comprising a combination of a discharge mechanism, a cartridge holder and a cartridge which is slidably accommodated in the cartridge holder. The cartridge comprises an ampoule containing one or more injection liquids, a piston movable in the ampoule and a hypodermic needle which is connected to the front of the ampoule and, if desired, is covered by a sheath to maintain the needle in a sterile condition. The discharge mechanism is provided with a power source which can move the cartridge from an inoperative to an operative condition. Also present are locking means for controlling the actuation of the power source and a safety device for blocking said locking device.

The automatic syringe of the invention is characterized in that it comprises a tablet holder which can contain one or more tablets.

The invention also relates to a tablet holder for the above syringe.

11 Claims, 4 Drawing Figures

AUTOMATIC INJECTION SYRINGE

The present invention relates to an automatic syringe in which an ampoule and a hypodermic needle in operative association therewith is driven by the force of a power source so as to insert the needle and then to inject the medicament or medicaments present in the ampoule.

This syringe comprises a combination of a discharge mechanism, a cartridge holder and a cartridge which is slidably accomodated in the cartridge holder said cartridge comprising an ampoule having one or more injection liquids, a piston which is movable in the ampoule, and a hypodermic needle connected to the front of the ampoule and covered, if desired, by a sheath to maintain the needle in sterile condition. The discharge mechanism is provided with a power source which can move the cartridge from the inoperative condition to the operative condition. Also present are locking means for controlling the actuation of the power source and a safety device for blocking said locking means.

Such a syringe is disclosed in Netherlands Patent Specification No. 160,725 in the name of Applicants.

Automatic syringes have been designed especially for use by persons who have to administer an injection into their own body at a given instant which is not known beforehand. These persons include, for example, soldiers after they have been exposed to an enemy's battle gas, for example, nerve gas. It will hence be obvious that high requirements have to be imposed upon automatic syringes as regards the reliability and ease of handling thereof. Such syringes are usually stored for years at a time and in addition are carried with the potential user for long periods of time under varying conditions; despite these facts the reliability of the syringe must remain ensured at the critical instant. When said critical instant has come, the syringe must be capable of being handled rapidly and easily and being used efficaciously.

All of these requirements are met by the automatic syringe described in the above-mentioned Netherlands Patent Specification No. 160,725.

However, many of the medicaments used in automatic syringes show undesired side effects or are insufficiently or incompletely active in therapeutical dosages. For example, the activity of medicaments which neutralize or control the toxic activity of battle gases, in particular nerve gases, is often incomplete. In an attack with nerve gas the primary medicament which is normally used is atropine or obidoxim, which substances counteract the toxic activity of organophosphate poisons, the active constituents of most nerve gases. However, these organophosphate poisons also cause paralyses or spasm conditions of the muscles which are insufficiently counteracted by the above-mentioned primary medicaments.

This disadvantage could be avoided by accommodating in the automatic syringe a secondary medicament which suppresses or counteracts the undesired side effect of the primary medicament or which completes or compensates for the insufficient or incomplete activity of the primary medicament, for example, while dissolved in the injection liquid in which the primary medicament is also dissolved. However, this is often not possible because these medicaments often are not compatible with each other during the long storage period, so that undesired reactions take place and the activity is reduced or is lost.

Another solution might be to accommodate in the automatic syringe the second medicament in the form of a second injection liquid to be injected separately. As a result of this, however, the syringe becomes particularly complicated in construction, while in addition not all medicaments are suitable for prolonged storage in a dissolved form suitable for injection, for example, in a physiological saline solution.

As a matter of fact it is not necessary to administer this secondary medicament simultaneously with the primary medicament. Of course, the primary medicament must be capable of being administered very quickly at the critical instant, preferably directly into the blood circulation system, so as to be active as rapidly as possible. However, the secondary medicament may also be administered orally in order to suppress or counteract the side effects of the primary medicament in good time, or to complete the insufficient or incomplete activity of the primary medicament.

It is the object of the present invention to provide an automatic syringe which can include a secondary medicament which is readily accessible so that it can easily be used orally.

For that purpose, the automatic syringe according to the present invention comprises a tablet holder which can contain one or more tablets of one or more secondary medicaments. For example, the activity of the atropine or obidoxim to be used against nerve gases is preferably completed by tablets containing benzodiazepines, for examples diazepam; simple derivatives of benzoic acid, for example 3-chloro-2,5,6-trimethyl benzoate, and other compounds such as germine mono acetate and 9-anthracene carboxylic acid also have the same favourable effect on the muscles. In addition to the above-mentioned therapeutic effect, diazepam also has a sedative influence, as a result of which the fighting value of the soldiers at the front is restored.

The tablet holder should be connected to the automatic syringe in such manner that a rapid administration of the primary medicament is not impeded. Speed is of the utmost importance in a life-threatening situation, so that any extra operation should be avoided when administering the primary medicament. Therefore, the tablet holder is preferably connected to the safety device of the syringe, so that the locking means are released simultaneously with the removal of the tablet holder.

The tablet holder preferably consists of two detachably connected parts, namely a tablet receiver which has a space for accommodating one or more tablets, and a sealing member to seal the receiver in an airtight manner.

An airtight sealing of the tablet holder is important because the syringe is often carried with the potential user under moist conditions and most tablets are of course moisture-sensitive (since they must disintegrate in the gastrointestinal tract).

In another preferred embodiment of the present invention, the tablet receiver is connected to the safety device, while the sealing member closes the receiver in a clamping manner. As in the syringe described in the above-mentioned Netherlands Patent Specification No. 160,725, the safety device can be removed from the syringe by exerting a backward directed force on the safety device. The tablet holder is then simultaneously removed while the locking means of the syringe are released. The syringe now is ready for use, in which the front of the syringe must be firmly pressed against the body at the place where the injection is to be administered. As a result of the exerted force, the locking of the power source is removed, after which the ampoule and needle move forward under the influence of the power source; the needle is inserted and the injection liquid with the primary medicament is injected. The user may then take the tablet (or tablets) from the tablet holder and swallow it (or them).

It is of advantage that the primary medicament is first administered before the tablet or tablets is or are swallowed. Therefore, the safety device of the syringe should preferably first detach when a backward directed force is exerted on the tablet holder connected to the safety device. Consequently, the holding force between safety device and syringe is preferably smaller than that between sealing member and tablet receiver. After administering the injection, the sealing member of the tablet receiver connected to the safety device may be removed, after which the tablet or tablets are released to be swallowed. It will be obvious that the holding force between safety device and tablet receiver preferably must be larger than that between safety device and syringe. The safety device and the tablet holder are rigidly connected together, for example, in that the latter is clamped around the former or in that they form one assembly.

In another preferred embodiment of the present invention the tablet receiver has the form of a hollow cylinder having a closed end the form is preferred and an open end, because this shape is best adapted to the shape of the tablets and because the open end of a cylindrical receiver can most easily be sealed in an airtight manner; the sealing member can then be clamped in or around the open end of the receiver by means of a skirt.

For a ready removal of the sealing member from the tablet receiver, said sealing member preferably has a finger grip, for example, in the form of a radially outwardly extending flange having a large diameter so that a soldier can easily open the tablet holder even with a gloved hand. The tablet receiver must preferably have a length such that the tablet or tablets cannot drop out of it prematurely and that there is sufficient space between the rear side of the syringe and the finger grip to be able to easily open the tablet holder with one finger, preferably the thumb.

In order to exclude mistakes in opening the tablet holder, the sealing member preferably has on its outside a projection in the form of a truncated cone. As a result of this the user will not be tempted to open the tablet holder by exerting pressure on the sealing member, while as a result of the truncation of the conical projection damage to clothing or gloves of the user is prevented.

Both the tablet receiver and the sealing member are normally manufactured from a synthetic resin material, the tablet receiver is manufactured from material which is deformation-proof, and consequently rigid, for example, polypropene; and the sealing member is manufactured from a slightly resilient material, for example, polythene (Lupolene), as a result of which it can be easily clamped around or in the open end of the tablet receiver so as to seal in an airtight manner.

For distinction between tablet receiver and sealing member, different colours may be used; for example, the receiver is preferably manufactured from clear transparent material so as to be able to readily observe the tablet or tablets, while the sealing member is preferably made of slightly coloured material, for example pale yellow.

In order to keep the tablet or tablets clamped against the closed end of the tablet receiver in the closed condition of the tablet holder, so as to avoid fracture of the tablet or tablets, the sealing member preferably has a rod-shaped body extending radially inward within the tablet receiver; the free end thereof extending entirely or substantially entirely against the tablet or tablets.

BRIEF DESCRIPTION OF THE DRAWINGS

The present invention will now be described in greater detail with reference to the drawing, in which.

Figure 1:
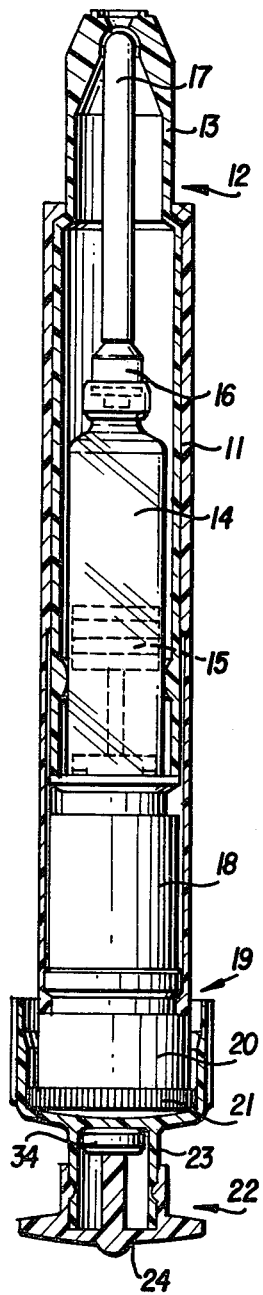
FIG. 1 is partly a longitudinal sectional view and partly an elevation of an automatic syringe according to the invention.

The embodiment shown in FIGS. 1, 2, 3 and 4 is only one example of the automatic syringe with tablet holder according to the present invention.

The syringe shown in the drawing is constructed for the greater part as described and shown in detail in Netherlands Patent Specification No. 160,725 in the name of Applicants.

In broad outline, the syringe comprises a cylindrical outer sleeve 11 in which a cartridge assembly 12 is provided so as to be slidable; said cartridge assembly comprising a cartridge holder sleeve or inner sleeve 13 fitting in the outer sleeve, a glass vial 14 with injection liquid, a piston 15 at one end and a needle mount 16 with injection needle having needle guard 17 at the other end of the vial. The cartridge assembly 12 is accommodated in the outer sleeve 11 in such manner that the closed end of the needle guard 17 bears against the apertured end of the cartridge holder sleeve 13. The outer sleeve 11 has a length such that the cartridge assembly 12 is accommodated in one end and the discharge mechanism 18 is accommodated in the other end. The discharge mechanism; whose power source is a coil spring; is the same as the spring power assembly described in the above-mentioned Netherlands Patent Specification No. 160,725, and comprises locking means not shown in the drawing and a safety member 19 which blocks the locking means. Both the locking means and the safety member are constructed as shown in Netherlands Patent Specification No. 160,725. The safety member 19 comprises a safety pin and a cap 20 which is connected thereto and has a milled edge 21. A tablet holder 22 consisting of a tablet receiver 23 and a sealing member 24 is connected to the rear side of the syringe.

The injection syringe may also include different injection liquids within the ampoule or vial, e.g. as described in the non-prepublished Netherlands patent application No. 8,103,744 in the name of Applicants. In that case, the different injection liquids may be separated from each other by means of stoppers, while in addition a by-pass is provided at the front side of the ampoule to enable a sequential delivery of the injection liquids upon actuation of the syringe.

Figure 2:
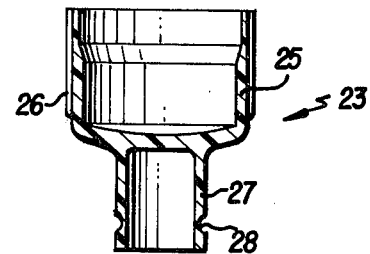
FIG. 2 is a longitudinal sectional view of a tablet receiver detached from the safety device of the syringe shown in FIG. 1.
Figure 3:
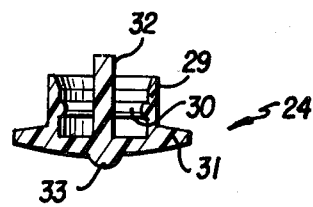
FIG. 3 is a longitudinal sectional view of a sealing member for said tablet receiver.

As is shown more clearly in FIG. 2, the tablet receiver comprises two coaxial cylindrical sleeve-shaped parts of which the closed ends partly coincide and the open ends face away from each other. One part 25 can be slid in a tight-fitting manner around the cap 20 of the safety member, so that a clamping connection is obtained. The milled edge 21 of the cap 20 ensures an extra rigid connection between the tablet receiver and the safety member, which cannot be broken when, for example, the safety member is removed from the syringe by means of a rotating movement. In another favourable embodiment of the present invention the tablet receiver and the safety member are integrally formed.

The cylindrical part 25 is provided externally with a knurled edge 26 so as to improve the grip. The other cylindrical part 27 of the tabler receiver is provided externally with a circumferential groove 28.

The sealing member 24 comprises a cylindrical sleeve-shaped part 29 which can be connected in a clamping manner around part 27 of the tablet receiver. Cylindrical part 29 has an internal circumferential locking ridge 30 which fits in the groove 28 of the tablet receiver. The sealing member further comprises a finger grip in the form of a radially outwardly projecting flange 31. The inner wall of the sleeve-shaped part 29 is slightly widened at the open end so as to facilitate the connection of the sealing member to the tablet receiver.

Figure 4:
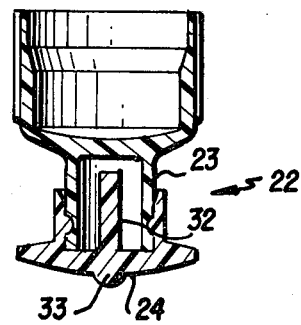
FIG. 4 is a longitudinal sectional view of the complete tablet holder.

The sealing member also comprises a rod-shaped member 32 which in the closed condition of the tablet holder extends aixially in the tablet receiver, as illustrated in FIG. 4. Furthermore, a projection 33 in the form of a truncated cone is present on the outside of the sealing member.

As shown in FIG. 1, one or more tablets 34 can be accommodated in the tablet holder.

When using the syringe according to the present invention, first the safety device plus tablet holder is removed. This is done by exerting a rearward directed force on the knurled sleeve-shaped part 25 of the tablet receiver or on the flange 31 of the sealing member. The safety pin is then dragged along out of the syringe, so that the locking means are released. At this point, an injection can be given with the syringe as described in the above-mentioned Netherlands Patent Specification No. 160,725.

The sealing member is now removed from the removed safety device plus tablet holder; this can be easily done with the thumb of the free hand, while the other hand holds the automatic syringe. With said thumb, i.e. the thumb of the same hand with which the knurled sleeve-shaped part 25 of the tablet receiver is held, the sealing member is pushed from the tablet receiver. The tablet holder is now opened so that the tablet or tablets contained in the holder can now be swallowed by bringing the opened tablet holder to the mouth.

I claim:

1. An automatic syringe comprising a combination of a discharge mechanism, a cartridge holder and a cartridge slidably accommodated in the cartridge holder; said cartridge comprising an ampoule containing at least one injection liquid, a piston movable in the ampoule and a hypodermic needle connected to the front of the ampoule; said discharge mechanism including a power source that can move the cartridge from an inoperative to an operative condition, locking means for controlling the actuation of the power source and a safety device for blocking said locking device, said syringe being characterized in that a tablet holder is connected to the safety device in a manner such that the locking means are released simultaneously with removal of the tablet holder.

2. A syringe as claimed in claim 1, wherein the cartridge further comprises a sheath that covers the needle and maintains the needle in a sterile condition.

3. A syringe as claimed in claim 1, wherein the tablet holder comprises two detachably connected parts, said parts comprising a tablet receiver having a space for accommodating at least one tablet and a sealing member to seal the receiver in an air-tight manner.

4. A syringe as claimed in claim 3, wherein the sealing member is connected to the tablet receiver in a clamping manner, the tablet receiver is connected to the safety device, and the locking means is released by removing the safety device.

5. A syringe as claimed in claim 4, wherein the holding force between the safety device and the syringe is less than that between the tablet receiver and the safety device, and also less than that between the sealing member and the tablet receiver.

6. A syringe as claimed in claim 4, wherein the tablet receiver and the safety device form one assembly, and the holding force between the safety device and the syringe is less than that between the sealing member and the tablet receiver.

7. A syringe as claimed in claim 4, wherein the tablet receiver comprises a hollow cylinder having a closed end and an open end, the sealing member being connected to said open end in a clamping manner.

8. A syringe as claimed in claim 7, wherein the sealing member further comprises a finger grip.

9. A syringe as claimed in claim 8, wherein the sealing member further comprises a projection in the form of a truncated cone on its exterior.

10. A syringe as claimed in claim 7, wherein the sealing member further comprises a rod-shaped member that extends axially within the tablet receiver and in the closed condition of the holder holds the tablet or tablets against the closed end of the tablet receiver.

11. A tablet holder adapted for attachment to an automatic syringe, comprising two detachably connected parts, said parts comprising a tablet receiver having a space for accommodating at least one tablet and a sealing member to seal the receiver in an air-tight manner, said tablet holder being characterized in that one of said parts includes connection means to connect the tablet holder to a safety device of the syringe.

* * * * *